United States Patent
Narayanan et al.

(10) Patent No.: US 9,713,452 B2
(45) Date of Patent: Jul. 25, 2017

(54) GENERATION OF MONOCHROMATIC IMAGES

(71) Applicant: GENERAL ELECTRIC COMPANY, Schenectady, NY (US)

(72) Inventors: Ajay Narayanan, Bangalore (IN); Bipul Das, Bangalore (IN); Vignesh Thirukazhukundram Subrahmaniam, Bangalore (IN)

(73) Assignee: General Electric Company, Niskayuna, NY (US)

( * ) Notice: Subject to any disclaimer, the term of this patent is extended or adjusted under 35 U.S.C. 154(b) by 199 days.

(21) Appl. No.: 14/230,852

(22) Filed: Mar. 31, 2014

(65) Prior Publication Data

US 2015/0272527 A1    Oct. 1, 2015

(51) Int. Cl.

| G06K 9/00 | (2006.01) |
|---|---|
| A61B 6/00 | (2006.01) |
| A61B 6/03 | (2006.01) |
| G06K 9/46 | (2006.01) |
| G06T 7/00 | (2017.01) |
| G06T 15/08 | (2011.01) |

(Continued)

(52) U.S. Cl.
CPC ............ *A61B 6/482* (2013.01); *A61B 6/032* (2013.01); *A61B 6/4241* (2013.01); *A61B 6/481* (2013.01); *A61B 6/5205* (2013.01); *A61B 6/5217* (2013.01); *G06K 9/46* (2013.01); *G06T 5/009* (2013.01); *G06T 5/50* (2013.01); *G06T 7/0012* (2013.01); *G06T 15/08* (2013.01); *A61B 6/4035* (2013.01); *A61B 6/5258* (2013.01); *G06T 2207/10072* (2013.01); *G06T 2207/10081* (2013.01); *G06T 2207/10116* (2013.01); *G06T 2207/20221* (2013.01); *G06T 2207/30004* (2013.01)

(58) Field of Classification Search
None
See application file for complete search history.

(56) References Cited

U.S. PATENT DOCUMENTS

| 3,508,047 A | 4/1970 | Mott et al. |
| 6,400,841 B1 * | 6/2002 | Khoury ................. G06T 7/0004 345/419 |
| 7,724,865 B2 | 5/2010 | Wu et al. |

(Continued)

FOREIGN PATENT DOCUMENTS

JP    2006090752 A    4/2006

OTHER PUBLICATIONS

Yu et al., "Virtual monochromatic imaging in dual-source dual-energy: Radiation dose and image quality", Medical Physics, vol. 38 No. 12, Nov. 9, 2011, pp. 6371-6379.*

(Continued)

*Primary Examiner* — Matthew Bella
*Assistant Examiner* — Jose M Torres
(74) *Attorney, Agent, or Firm* — Pabitra K. Chakrabarti (57) ABSTRACT

Identification of an optimal monochromatic energy for displaying monochromatic images is disclosed. In certain embodiments, determination of an optimal monochromatic energy may be performed by generating histograms for various monochromatic images generated based on a set of acquired multi-energy projections and by evaluating the histogram dispersion for the respective histograms.

20 Claims, 7 Drawing Sheets

(51) Int. Cl.
*G06T 5/00* (2006.01)
*G06T 5/50* (2006.01)

(56) References Cited

U.S. PATENT DOCUMENTS

| | | | |
|---|---|---|---|
| 8,363,917 B2 | 1/2013 | Fan et al. | |
| 8,494,244 B2 | 7/2013 | Dutta et al. | |
| 2006/0285630 A1* | 12/2006 | Bernhardt | G06T 11/005 378/4 |
| 2008/0273666 A1* | 11/2008 | Walter | A61B 6/4241 378/185 |
| 2010/0128844 A1* | 5/2010 | Thomsen et al. | 378/53 |
| 2010/0128942 A1* | 5/2010 | Licato et al. | 382/128 |
| 2011/0121163 A1* | 5/2011 | Kang | G01N 23/087 250/252.1 |
| 2011/0188725 A1* | 8/2011 | Yu et al. | 382/131 |
| 2011/0208058 A1* | 8/2011 | Hughes et al. | 600/443 |
| 2012/0039440 A1* | 2/2012 | Fan | A61B 6/032 378/62 |
| 2012/0135874 A1 | 5/2012 | Wang et al. | |
| 2013/0182927 A1* | 7/2013 | Jang et al. | 382/131 |
| 2013/0216113 A1* | 8/2013 | O'Connor | A61B 6/482 382/128 |
| 2014/0050378 A1* | 2/2014 | Sengupta | G06T 11/008 382/131 |
| 2014/0133729 A1* | 5/2014 | Goshen | G06T 5/002 382/131 |
| 2015/0178957 A1* | 6/2015 | Zou | G06T 11/005 382/131 |

OTHER PUBLICATIONS

Kumari et al., "Image Quality Estimation by Entropy and Redundancy Calculation for Various Wavelet Families", International Journal of Computer Information Systems and Industrial Management Applications, vol. 4, 2012, pp. 27-34.*
Kaza et al., "Distinguishing Enhancing From Nonenhancing Renal Lesions With Fast Kilovoltage-Switching Dual-Energy CT", Genitourinary Imaging, vol. 197, Issue 6, Dec. 2011.
Cheng et al., "Optimal Monochromatic Energy Levels in Spectral CT Pulmonary Angiography for the Evaluation of Pulmonary Embolism", PLoS one, vol. 8, Issue 5, 2013.

\* cited by examiner

GENERATION OF MONOCHROMATIC IMAGES

BACKGROUND

The subject matter disclosed herein relates to multi-energy imaging, including multi energy computed tomography (CT), and the generation of optimized monochromatic images in a multi-energy imaging context.

In X-ray based imaging systems, X-ray radiation spans a subject of interest, such as a human patient, and a portion of the radiation impacts a detector where the image data is collected. In digital X-ray systems a photo detector typically produces signals representative of the amount or intensity of radiation impacting discrete pixel regions of a detector surface. The signals may then be processed to generate an image that may be displayed for review. In computed tomography (CT) systems a detector array, including a series of detector elements, produces similar signals through various positions as a gantry is displaced around a patient.

In the images produced by such systems, contrast is created based upon the varying attenuation of the X-rays by the materials encountered as the X-rays penetrate the patient's tissue. Typically, materials having atoms with a greater atomic number will more strongly attenuate the passage of X-rays through the imaged volume. Thus, tissues such as bone may create relatively high contrast within an image compared to other tissues, such as fatty tissue. Some techniques used for X-ray based imaging use a contrast agent to artificially create contrast within an area that would typically not have relatively high contrast, such as blood vessels. The contrast agents may include one or more atoms capable of attenuating X-rays with a relatively high degree of efficiency, such as iodine. For example, in CT angiography, a contrast agent is typically injected into the patient, followed by CT imaging. The contrast agent typically perfuses through certain tissues of the patient, and the resulting CT images contain regions of enhanced contrast corresponding to the areas that are perfused with the contrast agent.

For typical single-energy X-ray based imaging, the resulting X-ray images are largely a representation of the average density of each analyzed voxel based upon the patient's attenuation of X rays emitted by the X-ray source and detected by the X-ray detector. However, for multi-energy X-ray imaging, a greater amount of imaging data may be gleaned for each pixel or voxel, such as an estimate of the type of material in each analyzed pixel or voxel. For example, in a dual-energy X-ray imaging system, X-ray spectra with two different energy distributions are employed. Higher-energy X-ray photons generally interact substantially less with patient tissue than the lower-energy X-rays. In the context of CT, in order to reconstruct multi-energy projection data, the underlying physical effects of X-ray interaction with matter are considered, namely, the Compton scattering effects and photoelectric effects, in a process known as material decomposition (MD). Using these techniques, it is possible to identify two or more constituent components in each analyzed voxel.

Thus, dual- or multi-energy imaging may offer the benefit of allowing tissue or material characterization. In certain contexts, such material decomposed images may allow for the generation of simulated monochromatic images, which depict the imaged region as it would appear if images using a single energy (keV) band, as opposed to a polychromatic spectrum of energy.

It has been observed, however, that such simulated monochromatic images vary in quality and do not necessarily have the desired image quality at those energy bands where good quality is expected. In particular, one variable that is outside the control of the person performing the scan is the variability introduced by the subject being imaged. That is, in a medical context, the patient undergoing imaging introduces variability in terms of their composition and path length that cannot be modeled or anticipated. This variability, therefore, can introduce variation in the observed signal-to-noise seen at the detector, even when the photon flux is kept constant during the scan. Further, some portion of this variability may manifest in scans obtained even at different energies, leading to correlated noise that observed at the different energies. Conversely, some portion of the noise observed at different energies will be uncorrelated. Taken together, this variability, whether due to variability introduced by the subject, drift introduced at the source, or noise effects introduced at the detector, can lead to image quality that is less than expected when generating simulated monochromatic images, even at a monochromatic energy that theoretically should yield the highest image quality.

BRIEF DESCRIPTION

In one embodiment, a method for determining an optimal monochromatic energy for all or a portion of a simulated monochromatic image is provided. In accordance with this method, steps are performed including accessing at least a first image acquired using a first polychromatic spectrum and a second image acquired using a second polychromatic spectrum. Material density maps are generated for at least two materials using the first image and the second image. A plurality of simulated monochromatic images are generated using the material density maps. Each simulated monochromatic image is at a different monochromatic energy. For the plurality of simulated monochromatic images, an optimal monochromatic energy is determined at which dispersion is minimized with respect to distributions generated using the simulated monochromatic images. Distributions may include empirical histograms, or fitted parametric distributions or fitted semi-parametric distributions, such as kernel density estimates where kernels can be multi-kernels. Examples of parametric distributions that could be fitted to a simulated monochromatic image measurements include, but are not limited to, the normal, log-normal, Rayleigh, Gamma, Weibull or Poisson distribution. Examples of non-parametric distributions that may be fitted to the data include, but are not limited to, kernel density estimates involving the Gaussian, Logistic, Haar, Epanechnikov kernels.

In a further embodiment, an image analysis system is provided. The image analysis system includes a memory storing one or more routines and a processor that executes the one or more routines stored in the memory. The one or more routines, when executed by the processor, cause the processor to: access at least a first image acquired using a first polychromatic spectrum and a second image acquired using a second polychromatic spectrum; generate material density maps for at least two materials using the first image and the second image; generate a plurality of simulated monochromatic images using the material density maps, wherein each simulated monochromatic image is at a different monochromatic energy; and for the plurality of simulated monochromatic images, determine an optimal monochromatic energy at which dispersion is minimized with respect to distributions generated using the simulated monochromatic images.

In an additional embodiment, a non-transitory, computer-readable media, encoding one or more processor-executable routines, is provided. The routines, when executed by a processor, causes acts to be performed including: accessing at least a first image acquired using a first polychromatic spectrum and a second image acquired using a second polychromatic spectrum; generating material density maps for at least two materials using the first image and the second image; generating a plurality of simulated monochromatic images using the material density maps, wherein each simulated monochromatic image is at a different monochromatic energy; and for the plurality of simulated monochromatic images, determining an optimal monochromatic energy at which dispersion is minimized with respect to distributions generated using the simulated monochromatic images.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As described in more detail below, provided herein are systems and methods for generating simulated monochromatic images in multi-energy X-ray imaging systems. As used herein, the term "simulated" monochromatic images may include numerically computed monochromatic images as well as monochromatic images that are physically measured or generated using reconstruction techniques. For example, during multi-energy CT projection data acquisition, a multi-energy X-ray source may be used to generate X-ray spectra having different energy distributions and may be capable of quickly switching from emitting a spectrum having a specific shape and/or mean energy to emitting a spectrum having a different shape and/or mean energy, such as by quickly modifying the peak operating voltage (kVp) of the X-ray tube or by applying different degrees or types of filtering. Once the X-ray source emits the X-ray spectrum containing a distribution of photon energies, these photons typically pass through a patient or object where they are partially attenuated before reaching an X-ray detector.

The projection data acquired at the different X-ray spectra may allow material density maps to be generated that can be used in tissue or material characterization and also in the generation of monochromatic images. As discussed herein, determination of an optimal monochromatic energy may be performed by generating histograms for various monochromatic images generated based on a set of acquired multi-energy projections and by evaluating the histogram dispersion for the respective histograms. Identification of the monochromatic energy (i.e., keV) where dispersion is minimized allows identification of an optimal monochromatic energy for the acquired set of multi-energy projections. For example, in one embodiment this may involve computing an entropy for each histogram or partial data histogram generated for each monochromatic image generated for a set of multi-energy (e.g., dual-energy) projections and identifying a global minima of entropy versus monochromatic energy. This global minima would identify the optimal monochromatic energy.

Knowing the optimal monochromatic energy may be desirable for various reasons. For example, the optimal monochromatic energy correlates to perceived image quality due to variations in the soft tissue regions being minimized at this monochromatic energy. In addition, small structure detectability is enhanced at this monochromatic energy.

Figure 1:
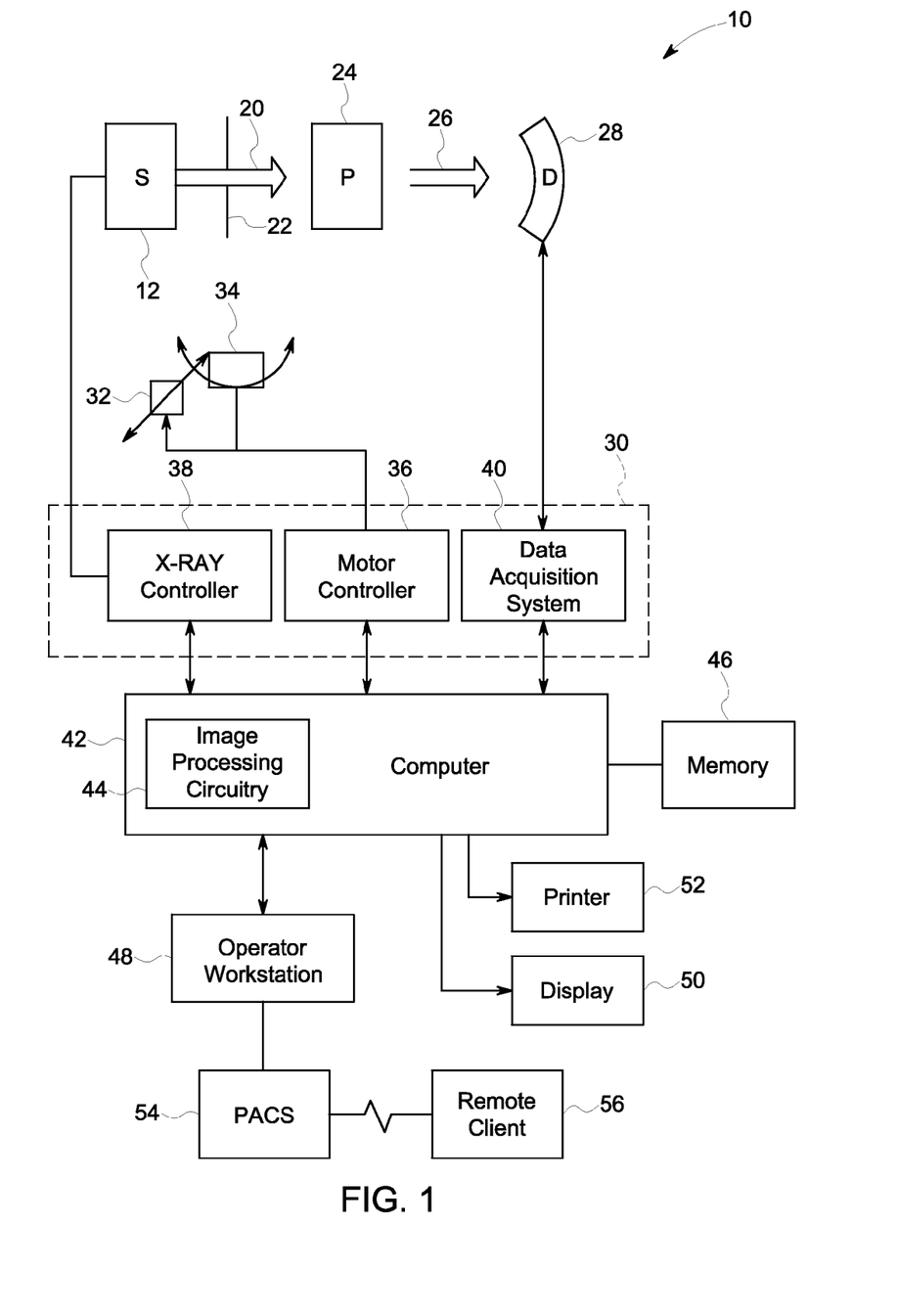
FIG. 1 is a schematic illustration of an embodiment of a computed tomography (CT) system configured to acquire CT images of a patient and process the images to determine an amount of a contrast agent within regions of the generated images.

With the preceding in mind, FIG. 1 illustrates an embodiment of a multi-energy imaging system 10 suitable for acquiring and processing image data to generate monochromatic images, as discussed herein. In the illustrated embodiment, system 10 is a computed tomography (CT) system suitable for acquiring X-ray projection data, reconstructing the projection data into tomographic images, and processing the image data for display and analysis. As will be appreciated, though a CT type system is provided as an example, the present approaches may be used in the context of other suitable imaging systems, such as other X-ray based systems suitable for acquiring images at various different energy spectra. Further, though the imaging system 10 is discussed in the context of medical imaging, the techniques and configurations discussed herein are applicable in other non-invasive imaging contexts, such as baggage or package screening in a security context and or quality-control in manufacturing or industrial context.

In the embodiment illustrated in FIG. 1, the CT imaging system 10 includes an X-ray source 12. As discussed in detail herein, the source 12 may include one or more X-ray sources, such as an X-ray tube. The X-ray source 12, in accordance with present embodiments is configured to emit an X-ray beam 20 having one or more possible energy spectra (e.g., a high energy and a low energy). For example, the X-ray source 12 may be configured to switch between relatively low energy polychromatic emission (e.g., having a mean around 40 kVp) and relatively high energy polychromatic emission (e.g., having a mean around 140 kVp). Such variable emission may enable the system 10 to perform material density measurements using, by way of non-limiting example, spectral emission.

The source 12 may be positioned proximate to a collimator 22 used to define the size and shape of the one or more X-ray beams 20 that pass into a region in which a subject 24 (e.g., a patient) is positioned. The subject 24, who may be treated with one or more contrast agent materials prior to imaging, attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more projection datasets.

As may be appreciated, the detector 28 may be of a variety of types while still falling under the scope of the present disclosure. By way of example, the detector 28 may be a conventional detector suitable for detecting X-rays at the energy levels emitted by the source 12 or may incorporate multiple panels or structures having different properties such that different panels or structures are employed for detecting X-rays having different energy spectra. Examples of possible detectors types include, but are not limited to: photon counting detectors, energy integrating detectors, and energy discriminating detectors.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, the X-ray controller 38 may be configured to switch the X-ray source 12 between different polychromatic emission spectra (e.g., high and low energy spectra) during operation. For example, emissions of the X-ray source 12 may be controlled so as to alternate between high energy spectrum emission and low energy spectrum emission.

The system controller 30 may also include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor of the computer 42. For example, a processor of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, execute image processing routines and algorithms, including algorithms for determining an optimal monochromatic energy and for generating a monochromatic image at the determined optimal energy, as discussed herein. For example, the memory 46 may store executable instructions for converting two polychromatic measurements to material decomposition pairs (e.g., a water-iodine pair) and in turn generating monochromatic images, the process of which may be referred to as spectral imaging (e.g., X-ray or CT spectral imaging). In this manner, a first monochromatic image at a first discrete energy and a second monochromatic image at a second discrete energy may be generated from two or more polychromatic image acquisitions. Generally stated, such spectral imaging techniques enable the simulation of an image that would be produced from a truly monochromatic acquisition (i.e., imaging at a single energy). Further stored and executable instructions may provide for the analysis of the monochromatic images and determination of an optimal monochromatic energy.

The computer 42 may also control operations enabled by the system controller 30 (i.e., scanning operations and data acquisition), such as in response to commands and scanning parameters provided by an operator via an operator workstation 48. The system 10 may include a display 50 coupled to the operator workstation 48 that allows the operator to view relevant system data, imaging parameters, raw imaging data, reconstructed data, simulated monochromatic images produced by the present approach, and so forth. Additionally, the system 10 may include a printer 52 coupled to the operator workstation 48 and configured to print generated images or image analysis results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
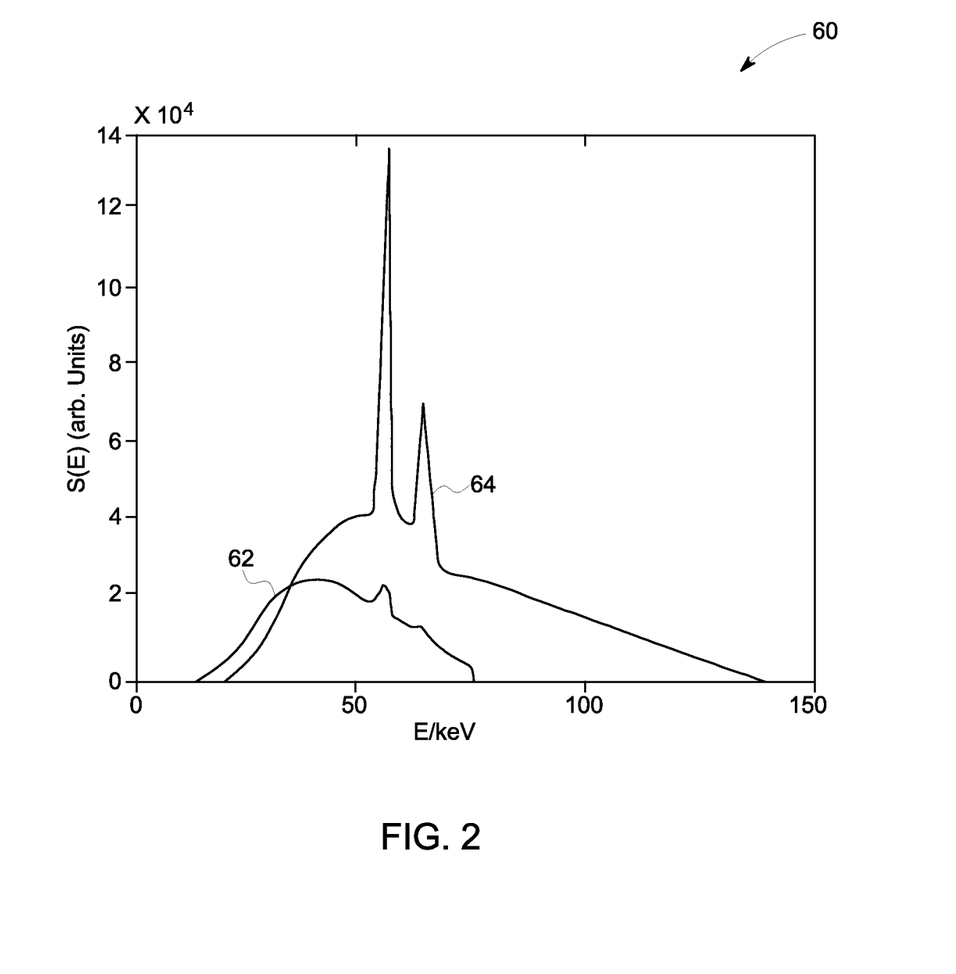
FIG. 2 is an embodiment of a plot of two different polychromatic source spectra generated by an X-ray source.

As noted above, the X-ray source 12 may be configured to emit X-rays at one or more spectra having different energy profiles. That is, emission at a single "energy" for the X-ray source 12 may constitute a polychromatic emission centered at, or having a peak or average strength at, the specified or representative energy. A plot 60 illustrating an example of two source spectra emitted by the X-ray source 12 of FIG. 1 is depicted in FIG. 2. Specifically, the plot 60 of FIG. 2 provides a first source spectrum 62 and a second source spectrum 64. The plot 60 depicts the strength of the first and second source spectra 62, 64 on the Y-axis as a function of an emitted energy on the X-axis.

As depicted, the first source spectrum 62 represents an emission by the X-ray source 12 of approximately 80 kVp, or peak kilovolts, which represents the highest energy emitted in the first source spectrum (i.e., low energy spectrum 62). In accordance with present embodiments, this represents a low energy emitted by the X-ray source 12, and may also be referred to as a low polychromatic energy emission or a low energy emission. The second source spectrum (i.e., high energy spectrum 64) represents an emission by the X-ray source of approximately 140 kVp. As may be appreciated, these two energy spectra may result in different images produced after X-ray imaging due to the differential transmission of X-rays corresponding to the different spectrum profiles. The images so produced may be composite images containing attenuation information across the entire source spectra, rather than at a discreet single energy.

In accordance with present embodiments, it may be desirable to generate, using images produced from at least the low and high energy spectra 62, 64 (or other separate and distinct energy spectra), simulated monochromatic images at an optimal monochromatic energy. With the preceding system discussion in mind, it should be appreciated that the present approach may be employed for various system or data acquisition scenarios. For example, the present approach may be applicable in dual-energy contexts, where data is acquired at a "low" and a "high" energy, as well as in contexts where data is acquired at more than two different energy spectra. Further, the present approach may be applicable for different spectrum shapes or distributions, such as where filtration may be employed to achieve a spectrum configuration, even if the average energy of the respective spectra are comparable. In addition, the present approach is applicable for different X-ray source and detector types. For example, the present approach may be employed with conventional radiographic detectors as well as with photon counting detectors, energy integrating detectors, and energy discriminating detectors.

As defined herein, a simulated monochromatic image is a representation or generated image corresponding to the image that would result if a true monochromatic source (i.e., a source that emits only one energy band) were employed as the source of X-ray emission. That is, the simulated monochromatic image corresponds to the image that would result if the X-ray emission from the source 12 were at a single, discrete keV value, as opposed to a polychromatic spectrum. In one embodiment, that simulated monochromatic image is produced by an image processing device based on at least two polychromatic images obtained using two different polychromatic energy spectra. As discussed below with respect to FIGS. 3-7, the present embodiments provide approaches for generating simulated monochromatic images and for determining an optimal monochromatic energy for simulating such a monochromatic energy.

Keeping in mind the operation of the system 10 and, specifically, the X-ray source 12 discussed above with respect to FIGS. 1 and 2, FIG. 3 illustrates a process flow diagram of an embodiment of an image processing method 80 for generating a simulated monochromatic image 86. Any suitable application-specific or general-purpose computer having a memory and processor or a comparable application specific integrated circuit (ASIC) may perform the method 80. By way of example, as noted above with respect to FIG. 1, the computer 42 and associated memory 46 may be configured to perform the method 70. For example, the memory 46, which may be any tangible, non-transitory, machine-readable medium (e.g., a disc, solid state device, chip, firmware), may store one or more sets of instructions that are executable by a processor of the computer 42 to perform the steps of method 80. In accordance with present embodiments, the processor, in performing method 80, may generate a simulated monochromatic image based on two or more polychromatic acquisitions.

Figure 3:
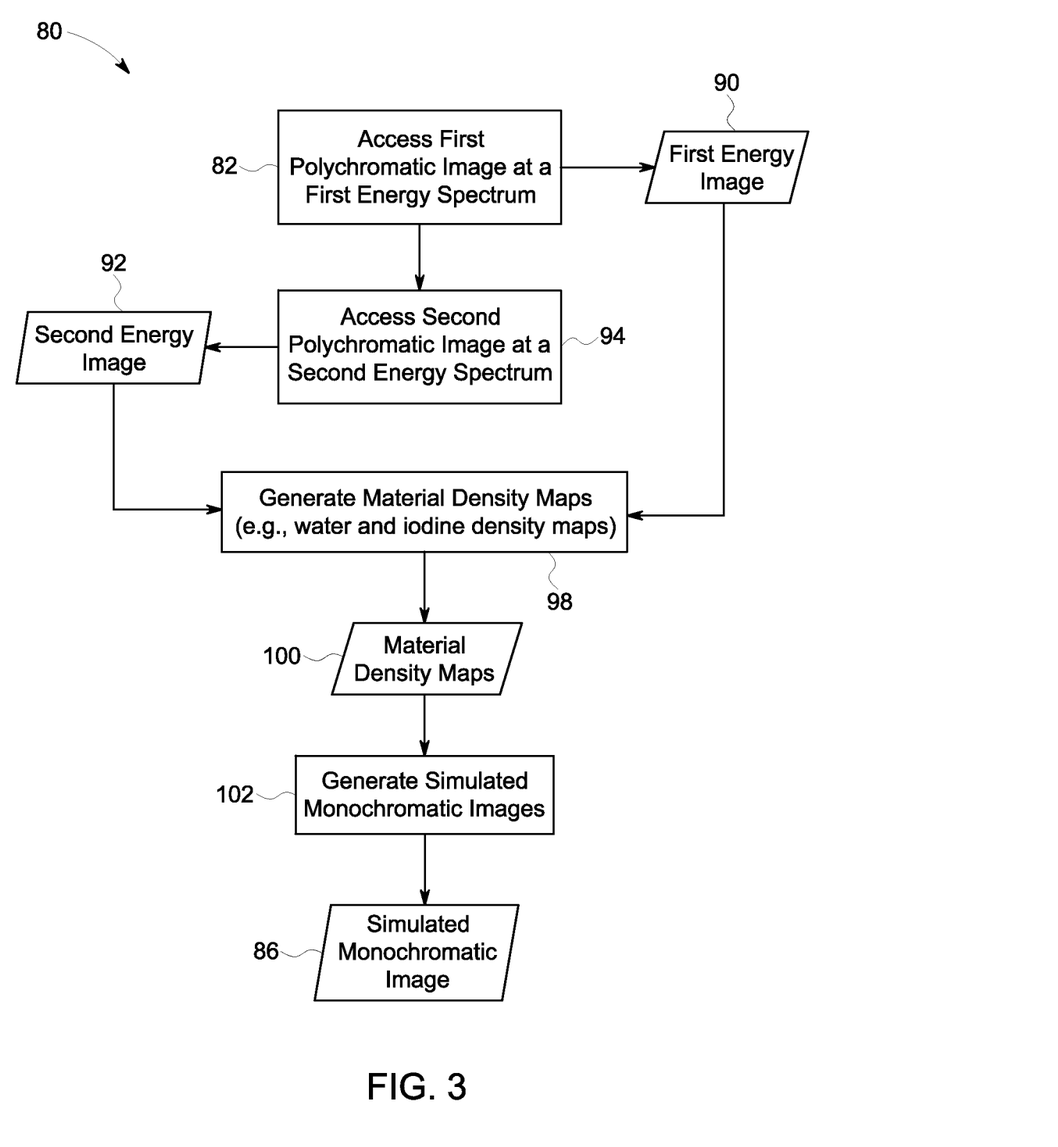
FIG. 3 is a process flow diagram depicting an embodiment of a generalized process for generating a simulated monochromatic image, in accordance with aspect of the present disclosure.

The method 80 includes accessing (block 82) a first polychromatic X-ray image (e.g., first energy image 90, such as a low-energy image) using a first X-ray energy spectrum that is polychromatic (e.g., a low-energy spectrum 62). A second polychromatic X-ray image (e.g., second energy image 92, such as a high-energy image) is also accessed (block 94) using a second polychromatic X-ray energy spectrum (e.g., a high-energy spectrum 62). As noted above, in other embodiments, additional images acquired using different energy spectra may also be included. In one embodiment, one or both of the images 90, 92 may be contrast-enhanced, such as due to a contrast agent (e.g., a vascular contrast agent such as iodine) being administered to the subject prior to image acquisition. As will be appreciated, accessing one or both of the images 90, 92 may involve acquiring the images by performing a dual- or multi-energy image acquisition protocol using an imaging system 10 or may involve accessing the images from a storage medium, such as from a system memory, a local or network accessible storage device, or from an image archiving system, such as the PACS 54 of FIG. 1. Therefore, the acts associated with accessing the images 90 and 92 may be performed by the system 10, or by a computing device local to or remote from the facility in which the image is acquired.

Using the first energy image 90 and second energy image 92, material density maps or images 100 may be generated (block 98). A simulated monochromatic image 86 at a given energy band (keV) may be generated (block 102) based upon the respective material density maps (i.e., material decomposed images) to yield the desired energy band.

Figure 4:
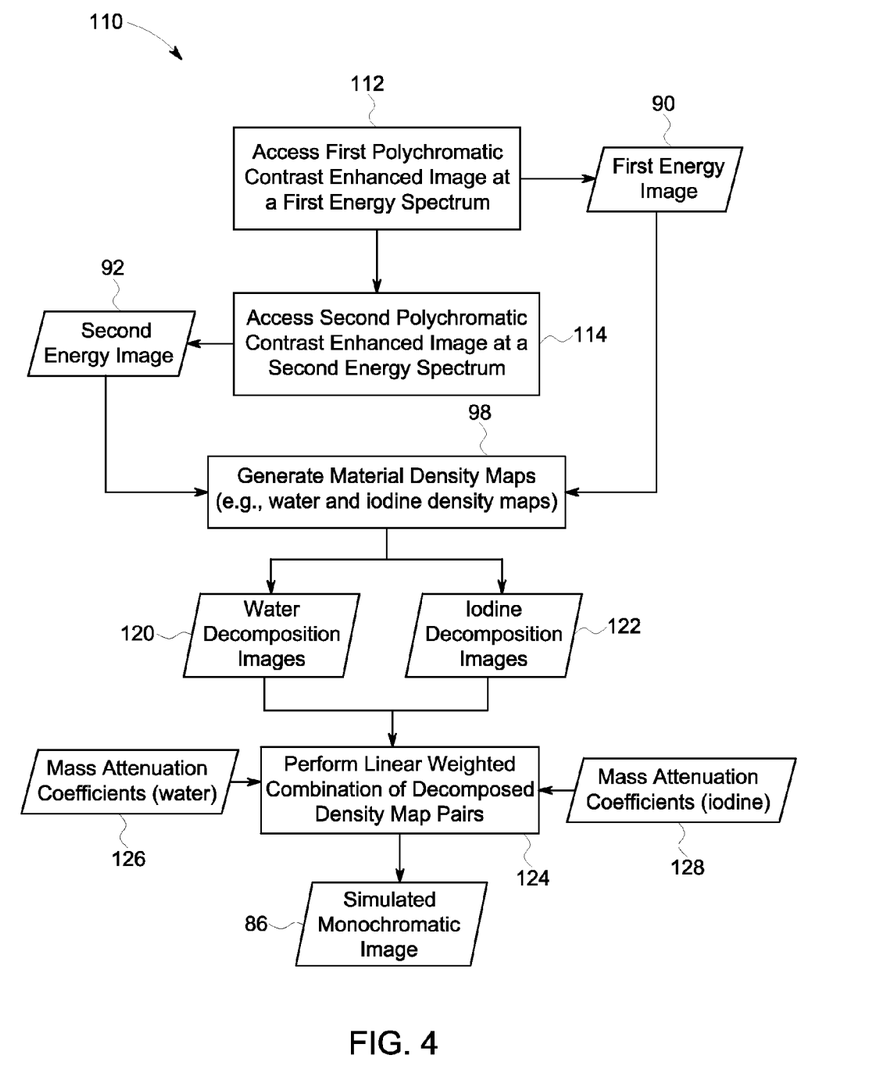
FIG. 4 is a process flow diagram depicting a further embodiment of a process for generating a simulated monochromatic image, in accordance with aspect of the present disclosure.

A more detailed example of one such process is illustrated in FIG. 4, which depicts a further process flow diagram. In this example, as in the prior, a method 110 is provided where a first polychromatic X-ray image (e.g., first energy image 90, such as a low-energy contrast-enhanced image) is accessed (block 112) using a first X-ray energy spectrum that is polychromatic (e.g., a low-energy spectrum 62). A second polychromatic X-ray image (e.g., second energy image 92, such as a high-energy contrast-enhanced image) is also accessed (block 14) using a second polychromatic X-ray energy spectrum (e.g., a high-energy spectrum 62). In one embodiment, both of the images 90, 92 are contrast-enhanced, such as due to a contrast agent (e.g., a vascular contrast agent such as iodine) being administered to the subject prior to image acquisition.

In this example, the respective first energy images 90 and second energy images 92 are used to generate respective water decomposition images 120 and iodine decomposition images 122 (i.e., material decomposition images), which respectively depict (or map) the respective densities of water and iodine in the imaged regions. In the depicted example, the respective material decomposed density map pairs (here denoted as water decomposition images 120 and iodine decomposition images 122) may then undergo a linear weighted combination (block 124) which leverages the respective mass attenuation coefficients 126, 128 of water and iodine to generate a simulated monochromatic image 86 at a given energy band (keV). In particular, the weighting used in the linear combination are the mass attenuation coefficients 126, 126, of water and iodine in this example.

With the preceding in mind, it may be noted that the noise in the density image pairs is believed to be generally negatively correlated. In particular, the correlations are theoretically expected to cancel out at about 70 keV in certain imaging systems. In practice, however, it has been observed that the best perceived image quality for simulated monochromatic images generated in accordance with the preceding approaches may generally be in the range of 65 keV to 85 keV. Such variations in image quality about the theoretical optimum of 70 keV may be attributed to a variety of factors, including, but not limited to, scanner drifts, source spectra shifts, subject induced spectral shifts, and so forth. In particular, one aspect of an image acquisition that is outside of the control of the technician is the variability introduced by the subject (e.g., patient) undergoing imaging, who may introduce a variety of anatomical and physiological uncertainties related to path length and composition. Such uncertainties may be generally unknown and, thus, not subject to modeling. As a result, even if a technician has complete control over those parameters related to the system acquiring images, there will still be uncertainty introduced due to the nature of the subject being imaged. Such subject-specific uncertainties may lead to signal noise having both correlated and uncorrelated components in the data acquired using different spectra. As a result, simulated monochromatic images generated using such data may be perceived as having a sub-optimal image quality and resolution when compared to comparable dose-neutral single energy polychromatic CT scans of the same subject, even when the simulated monochromatic image is generated for a theoretical ideal monochromatic energy.

As may be appreciated, a corollary to this observation is that, for a given multi-energy data acquisition, a single monochromatic energy does exist at which the correlated component of the noise in the paired material density maps (e.g., water-iodine maps) is maximally canceled. As used herein, this monochromatic energy is referred to as the optimal monochromatic energy and a monochromatic image simulated at this optimal energy is referred to herein as the optimal monochromatic image.

As discussed herein, an automated approach to identifying the optimal monochromatic image is provided. This approach is in contrast to approaches in which a user interactively changes the displayed monochromatic energy and image (i.e., a manual process) to visually identify a satisfactory monochromatic image, such as based on the perceived smoothness of homogeneous tissue regions. Such manual approaches suffer from lack of repeatability and from a failure to reliably identify an optimal monochromatic energy or image, as used herein.

The foundation of the present approaches is based on various observations. First as noted above, it is assumed that there exists an optimal monochromatic energy and image. In particular, for two polychromatic scans acquired using different energy spectrum profiles, a monochromatic energy exists at which homogeneous tissue responses have the least variation.

This proposition is supported based on a number of observations. First, noise in the material decomposition images (e.g., water decomposition image 120 and iodine decomposition image 122) is known to be negatively correlated. These correlations result in a variation in the iodine responses for a given single water density measurement. As noted above, monochromatic images 86 are simulated using the density maps by performing a weighted addition of responses, in which the mass attenuation coefficients $\mu_m(E)$ of water and iodine are the weights (assuming an embodiment where water-iodine are used for the density map pairs). At a particular monochromatic energy, underestimation at a voxel in the iodine map and the corresponding overestimation in the water map cancel out due to the non-linear nature of the $\mu_m$-curves as a function of different energies. The values of the mass attenuation at this particular monochromatic energy are such that they appropriately compensate for the correlation between the measured density values. The effect of the correlated noise is an increased dispersion (e.g., standard deviation) about a voxel in a homogeneous region of the corresponding monochromatic image at that particular energy. Therefore, the monochromatic energy (and corresponding image) that produces the minimal variation would in effect have the best perceived image quality (e.g., better homogeneity of soft tissues, contrast-enhanced cardiac chambers, and so forth). Thus, there exists an optimal monochromatic energy that corresponds to the production of this minimal variation about a voxel in a homogeneous region of a corresponding monochromatic image.

Based on the existence of an optimal monochromatic energy, the present approach attempts to leverage this knowledge to identify the optimal monochromatic energy for a given set of scans. In particular, as noted above the optimal monochromatic energy has the best cancellation of the correlated effects of the material density measurements. Thus, all image regions having a single tissue response having associated flat spectral $\mu_m$ curves would have the least variation at this monochromatic energy. As will be appreciated, having the least variation in the image voxel domain also translates to having a minimal histogram variation about the mode corresponding to this tissue. It is thus possible to use any metric that captures histogram dispersion as a feature to determine the optimal monochromatic energy.

Figure 5:
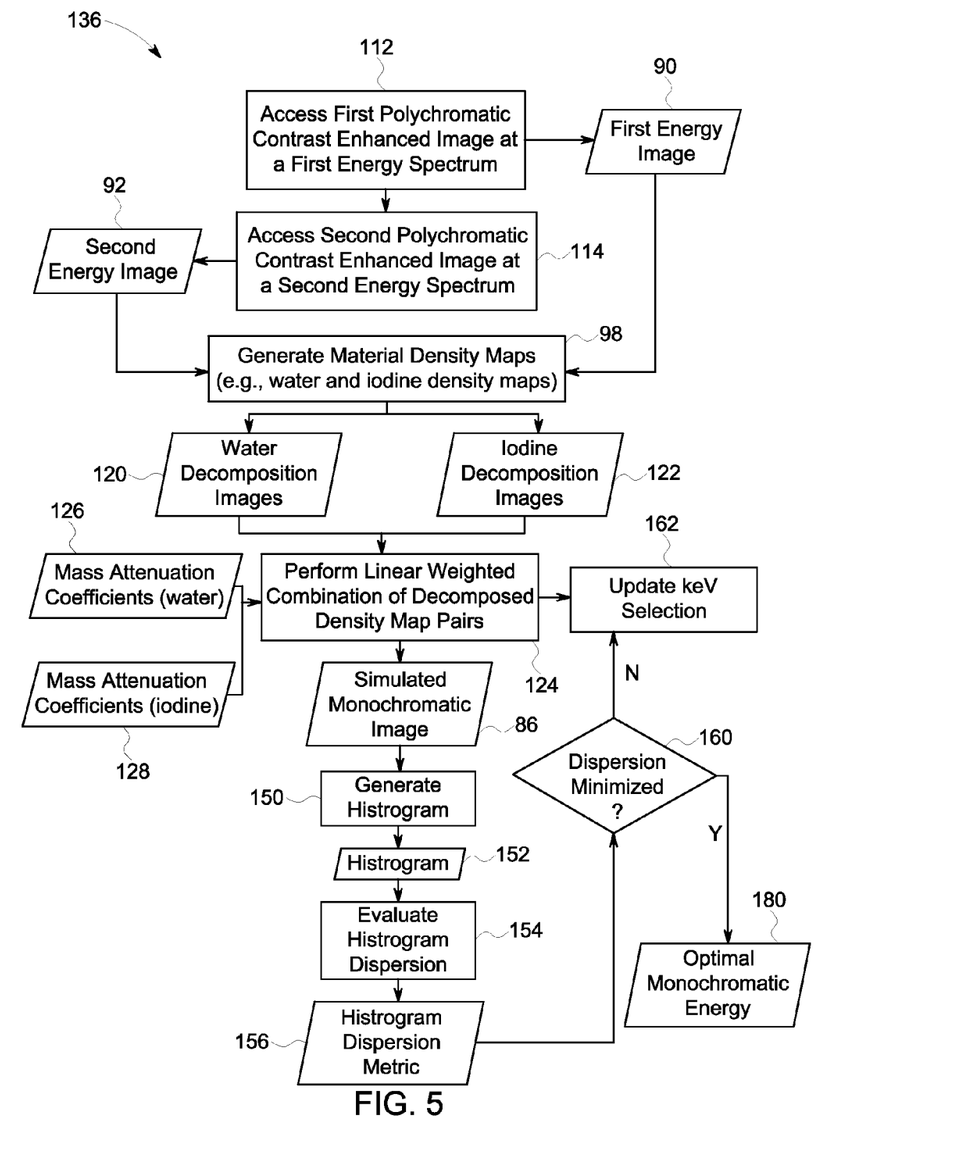
FIG. 5 is a process flow diagram depicting an embodiment of a generalized process for determining an optimal monochromatic energy, in accordance with aspect of the present disclosure.

An example of a generalized process-flow 136 illustrating one such embodiment is provided in FIG. 5. In this example, the simulated monochromatic image 86 generated at a given monochromatic energy (i.e., keV) us processed to generate (block 150) a histogram 152. The dispersion of the histogram is evaluated (block 154), resulting in one or more histogram dispersion metrics 156 being generated. A determination (block 160) may be made as to whether a given dispersion metric 156 is minimized. If the dispersion metric 156 is determined to be minimized, the corresponding monochromatic energy for the respective simulated monochromatic image 86 is determined to be the optimal monochromatic energy 180, and the respective simulated monochromatic image is, correspondingly, the optimal monochromatic image. Conversely, if the dispersion metric is not determined to be minimized, the keV (i.e., monochromatic energy) may be iterated to a next value (such as a next value in a sequence ranging from 40 keV to 140 keV) and the process repeated until a minimized dispersion metric 156 is identified. As will be appreciated, though a sequential analysis is depicted in FIG. 5 for the purpose of illustration and explanation, in other embodiments or real-world implementations, a set of simulated monochromatic images 86 may instead be initially generated over a range of interest (such as over a range from 40 keV to 140 keV) and each simulated monochromatic image 86 analyzed to determine the optimal monochromatic energy 180.

One example of a suitable metric is the Shannon entropy, defined as:

$$e = -\Sigma_i p_i \ln(p_i). \quad (1)$$

where e is the Shannon entropy, p is the proportion of observations in the i-th cell of an empirical histogram. The Shannon entropy is minimized when the dispersion of a unimodal histogram is minimized. Thus, finding a minimum for Shannon entropy may be useful for identifying an optimal monochromatic energy assuming that entropy minimization is comparable to dispersion minimization. This is believed to be a reasonable assumption in that entropy minimization can be used to sharpen an image, even if two different (but spectrally similar materials) are present, by sharpening the modes of the bi-modal histogram. Conversely, dispersion minimization, in such a context, will lead to an energy in which the two materials have the least separation, which may have adverse effects on the diagnostic utility of an image. Thus, the monochromatic energy at which the noise correlations for two materials cancel out (i.e., the optimal monochromatic) results in a simulated monochromatic image that has a minimized entropy metric (such as Shannon entropy) in histogram space. That is, a histogram will have a higher entropy if the noise correlations are unbalanced, such as in a water-iodine weighted sum, at any monochromatic energy that is not the optimal monochromatic energy. Thus, based on this observation, a minimized entropy metric, such as a minimum Shannon entropy can be used to determine an optimal monochromatic energy.

While the Shannon entropy is one possible entropy metric, other metrics may instead be employed. Examples of other suitable metrics include, but are not limited to, the use of relative entropy, such as through the use of the Kullback-Leibler divergence, and generalizations of the Shannon entropy, such as the Renyi entropy. The Renyi entropy is given by:

$$e_r = \frac{1}{1-\alpha} \log\left(\sum p_i^\alpha\right) \quad (2)$$

where $\alpha$ is a positive number not equal to 1. As will be appreciated, when $\alpha$ approaches 1, the Renyi entropy is the Shannon entropy. However, when $\alpha$ is less than 1, the Renyi entropy measure may help emphasize the contribution of less dominant modes in the histogram to the entropy.

Figure 6:
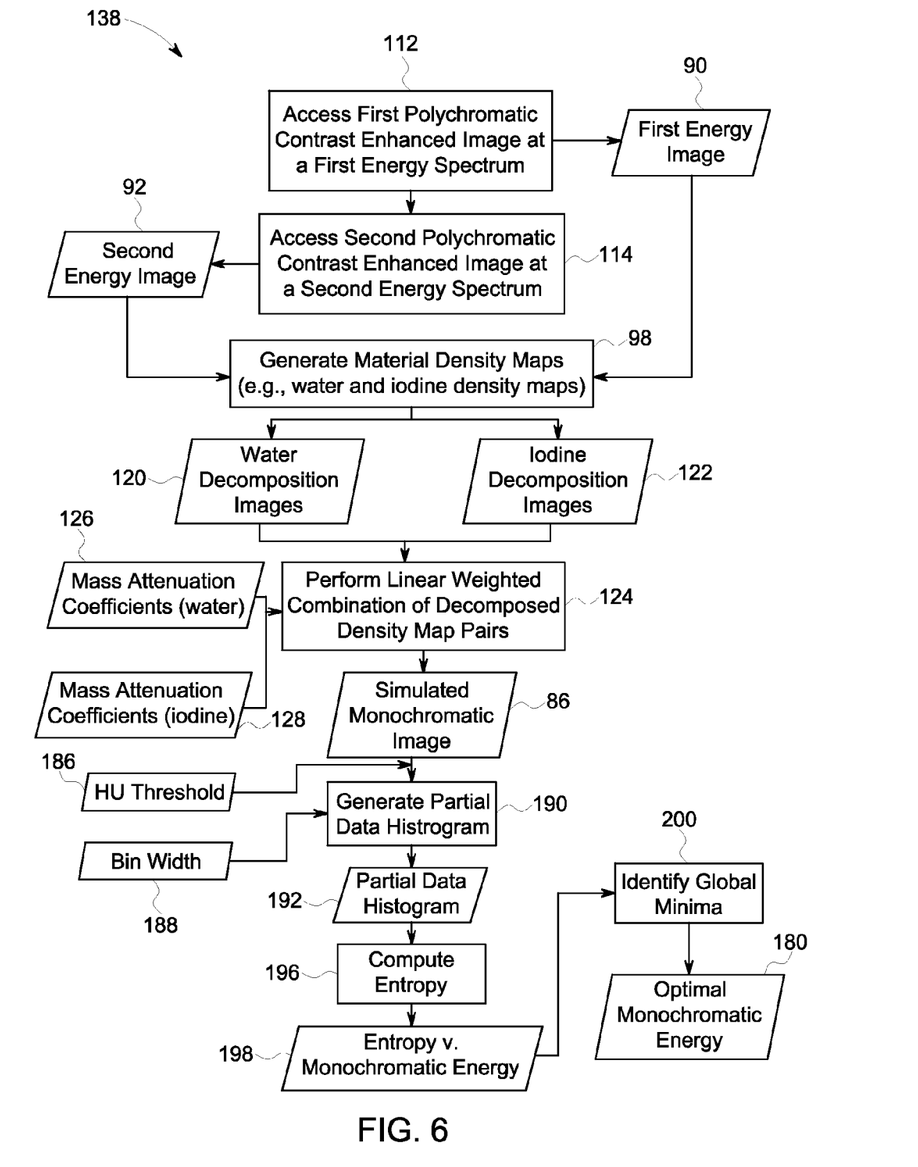
FIG. 6 is a process flow diagram depicting a further embodiment of a process for determining an optimal monochromatic energy, in accordance with aspect of the present disclosure.

As will be appreciated from the preceding discussion, the isolation of spectrally flat tissues may be important as the proposition that the optimal monochromatic energy has the minimum Shannon entropy is true only when computed over tissues that are unimodal and that have low dispersions in their true densities. Thus, in certain embodiments it may be desirable to exclude regions of bone from the entropy analysis due the density variation such bone regions exhibit in CT images. In one implementation, to achieve sharper metric minima, air, fat, and soft-tissue regions maybe isolated by partitioning the image data of the nominal monochromatic image into two compartments based on a threshold intensity criterion (e.g., 100 HU). That is, the image data is binned such that voxel having an intensity value less than 100 HU are assigned to a first bin (i.e., a bin for air, fat, and soft tissue regions) and voxels having an intensity value of 100 HU or greater are assigned to a second bin (i.e., bone). In this manner, the flat response tissues may be isolated and used in subsequent processing, while those regions exhibiting variable response may be excluded from the subsequent analysis. Turning to FIG. 6, an example process flow 138 is depicted where such a HU threshold 186 is employed to partition the monochromatic image 86 prior to generating (block 190) a partial data histogram 192 based on this thresholded data.

With respect to the generation (blocks 150, 190) of the histograms 152, 192, one consideration is the bin width 188 used in generating the histogram. In particular, in embodiments where Shannon entropy is employed as an entropy metric, the Shannon entropy may be sensitive to the binning of the histogram. Employing variable bin-width to optimize the tradeoff between histogram smoothness and fidelity may be one option. However, the effects of correlated response induced artifacts may tend to shift the monochromatic response in small HU increments about the ideal tissue response mode. Therefore, in certain implementations it may be desirable to instead keep the bin width constant to improve detectability of correlation induced frequency drifts in the histogram 152, 192. By way of example, in one implementation, a bin width between about 3 HU and 7 HU is employed (such as 3 HU, 4 HU, 5 HU, 6 HU, 7 HU), though other constant bin widths may instead be employed, as may variable bin widths. In general, it may be desirable to choose bin width so as to ensure sufficient variability of the entropy metric around the minima to provide metric sharpness while simultaneously providing histogram smoothness.

Turning back to FIG. 6, once the spectrally flat response tissue candidate voxels have been identified (e.g., by application of HU threshold 186) and the bin width 188 specified, respective partial data histograms 192 at different monochromatic energies may be analyzed (such as over a range from 40 keV to 140 keV). For example, in one implementation an entropy measure (such as the Shannon entropy) is calculated (block 196) for the respective partial data histogram 192 at each monochromatic energy within the desired range. A measure of entropy versus monochromatic energy 198 may then be computed and a global minima identified (block 200). The monochromatic energy corresponding to the identified global minima of the entropy measure is, in one such embodiment, the reported optimal monochromatic energy 180.

It should also be mentioned that, though the present discussion and preceding examples are presented in the context of a simulated monochromatic image 86, it should be appreciated that such an image may encompass a range of volumetric representations, including a volume or object undergoing imaging, a slice or two-dimensional image through such a volume, a sub-volume within the larger whole volume, or a sub-region of a two-dimensional image or slice, down to the voxel level. That is determination of an optimized monochromatic energy may be performed for a range of volumes spanning a single voxel up through an entire imaged volume, including for slices or images through the larger volume. Thus, in the context of the present disclosure an optimal monochromatic energy may be determined for an entire volume and the entire volume represented at that determined optimal monochromatic energy in the image 86. At the other extreme, an optimal monochromatic energy may be determined for each voxel of a volume or slice, with the resulting image composed of a multitude of voxels that are each individually at their respective optimal monochromatic energy. Between these extremes, the optimal monochromatic energy may be determined for a slice through a volume, for a sub-volume of a larger volume (such as for a portion of the volume corresponding to a particular organ or tissue type or any arbitrary voxel in the volume or a set of local or non-local set of voxels). As a result, optimization of the monochromatic energy for a simulated monochromatic image 86, as discussed herein, should be understood as encompassing determining an optimal monochromatic energy for a range of volumes, from a voxel and larger.

The preceding approach was experimentally tested using various phantom and clinical data sets. Optimal monochromatic energy determined (at mid-Z slice) for the various clinical and phantom scans is given by Table 1.

TABLE 1

| Object | Optimal keV |
|---|---|
| Excised Plaque | 58 |
| Clinical- Head/Neck CTA | 65 |
| Clinical - Head CTA | 69 |
| Phantom (Pig Liver) | 74 |
| Clinical - Head CTA | 82 |
| Clinical - Cardiac | 83 |

Figure 7:
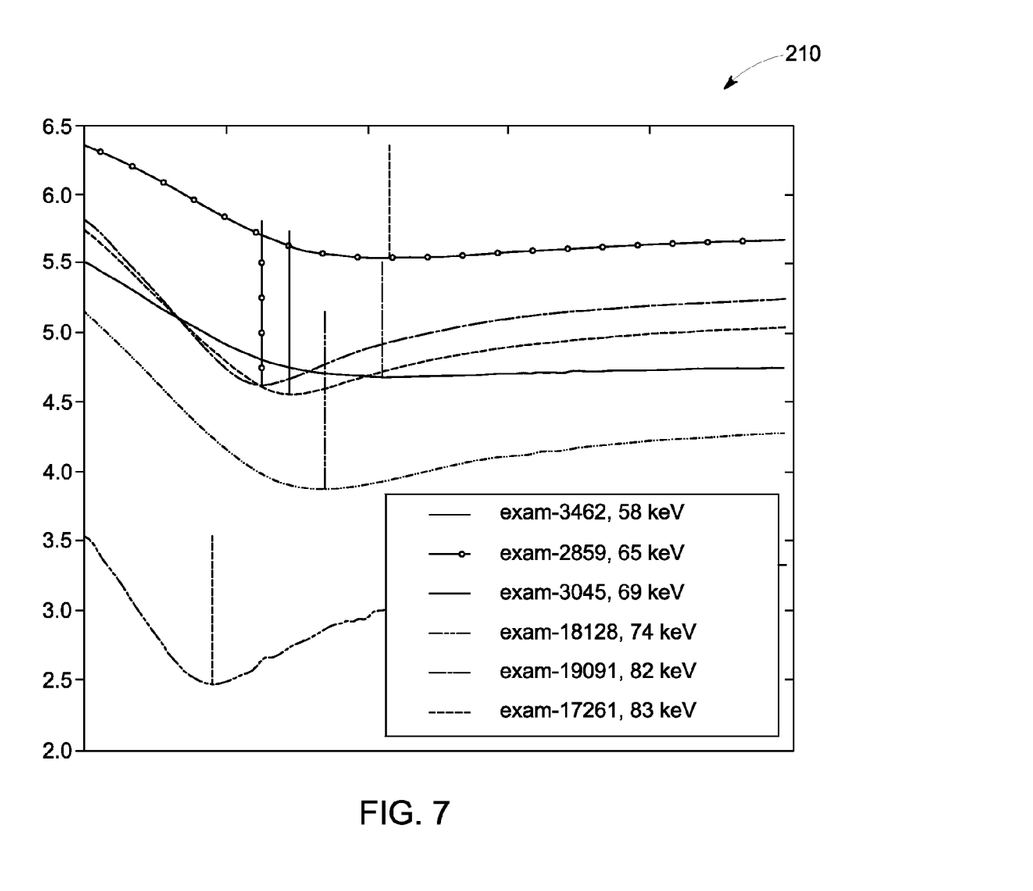
FIG. 7 is a plot of entropy versus monochromatic energy for various studies conducted in accordance with aspect of the present disclosure.

Turning to FIG. 7 the respective plots 210 of entropy vs. monochromatic energies for the studies of Table 1 are illustrated. In particular, FIG. 7 shows the mid-Z slice entropy curves across monochromatic energies. Each plotted curve represented a study from Table 1 while the intersection of the vertical bar on each curve represented the identified entropy minima. The legend of the plot identifies the minima energy value, corresponding to the values provided in Table 1.

As may be appreciated, in practice the optimal monochromatic energy may vary within the imaged volume, such as along the Z-direction. As a result, slices taken at different Z-locations relative to the mid-Z slice may differ in their optimal monochromatic energy. Likewise, different structures within the imaged volume, such as different organs or tissue types may differ in their optimal monochromatic energy. As a result, a simulated monochromatic image 86 reproduced for a portion of a volume or slice may benefit from being displayed as a different optional monochromatic energy than other portions of the volume or slice.

One consequence of these differences is that the present approach may be used to generate an energy map and/or a monochromatic energy recommendation, such as for different organs or tissue types present in an imaged volume. Likewise, the present approach may be useful for detecting regions of interest (e.g., hotspots) within a given data set where an expectation for the optimal monochromatic energy does not correspond to what is observed. For example, calcifications or plaques present in a tissue may skew the optimal monochromatic energy toward what would be expected in the presence of calcium, as opposed to the values expected for normal, healthy tissue. Such deviations may be useful for highlighting regions for further examination by a clinician.

Technical effects of the invention include, but are not limited to, automatically determining an optimal monochromatic energy for the display of a simulated monochromatic image generated using two or more polychromatic X-ray images. The determination of the optimal monochromatic image may involve performing an evaluation of histogram dispersion for histograms generated based on one or more simulated monochromatic images generated over a range of monochromatic energies. In certain implementations, this may include the determination of an entropy metric for simulated monochromatic images at each energy and a determination of a global minima with respect to the entropy metric. Simulated monochromatic images generated at the optimal monochromatic energy may have a higher perceived image quality due to variations in the soft tissue regions being minimized and due to improved detectability of small structures.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining an optimal monochromatic energy for all or a portion of a simulated monochromatic image, the method comprising:
   accessing at least a first image acquired using a first polychromatic spectrum and a second image acquired using a second polychromatic spectrum;
   generating material density maps for at least two materials using the first image and the second image;
   generating a plurality of simulated monochromatic images using the material density maps, wherein each simulated monochromatic image is at a different monochromatic energy;
   generating a respective histogram for each simulated monochromatic image, wherein each histogram is characterized by a respective dispersion;
   for each histogram, deriving a quantitative metric characterizing the respective dispersion;
   evaluating the quantitative metrics of the histograms to determine the histogram where dispersion is minimized; and
   identifying the monochromatic energy corresponding to the histogram where dispersion is minimized as a target monochromatic energy at which homogeneous tissue responses have the least variation.

2. The method of claim 1, wherein the simulated monochromatic images correspond to all or part of an imaged volume, and wherein the simulated monochromatic images are numerically computed or are physically measured or generated using reconstruction techniques.

3. The method of claim 2, wherein the simulated monochromatic images correspond to a voxel, all or part of a slice, or a sub-volume of the imaged volume.

4. The method of claim 1, wherein determining the target monochromatic energy comprises:
   computing an entropy metric as the quantitative metric for each distribution; and
   identifying a minima in entropy with respect to monochromatic energy as the act of evaluating the quantitative metrics, wherein the minima is indicative of the target monochromatic energy.

5. The method of claim 1, further comprising displaying a simulated monochromatic image at the target monochromatic energy.

6. The method of claim 1, further comprising displaying the target energy at every voxel for a sub-volume of an imaged volume.

7. The method of claim 1, wherein generating the plurality of simulated monochromatic images comprises performing linear weighted combinations of the material density maps using the respective mass attenuation coefficients of respective materials as weights.

8. The method of claim 1, wherein the target monochromatic energy corresponds to the monochromatic energy at which, for the first image and the second image, one or more homogeneous tissue responses have the least variation.

9. The method of claim 1, wherein the monochromatic energy cancels correlated effects of material density measurements.

10. An image analysis system, comprising:
a memory storing one or more routines; and
a processor that executes the one or more routines stored in the memory, wherein the one or more routines, when executed by the processor, cause the processor to:
access at least a first image acquired using a first polychromatic spectrum and a second image acquired using a second polychromatic spectrum;
generate material density maps for at least two materials using the first image and the second image;
generate a plurality of simulated monochromatic images using the material density maps, wherein each simulated monochromatic image is at a different monochromatic energy;
generate a respective histogram for each simulated monochromatic image, wherein each histogram is characterized by a respective dispersion;
for each histogram, derive a quantitative metric characterizing the respective dispersion;
evaluate the quantitative metrics of the histograms to determine the histogram where dispersion is minimized; and
identify the monochromatic energy corresponding to the histogram where dispersion is minimized as; a target monochromatic energy at which homogeneous tissue responses have the least variation.

11. The image analysis system of claim 10, wherein the simulated monochromatic images correspond to a voxel, all or part of a slice, or a sub-volume of an imaged volume.

12. The image analysis system of claim 10, wherein determining the target monochromatic energy comprises:
computing an entropy metric as the quantitative metric for each distribution; and
identifying a minima in entropy with respect to monochromatic energy as the act of evaluating the quantitative metrics, wherein the minima is indicative of the target monochromatic energy.

13. The image analysis system of claim 12, wherein the entropy metric includes one or more of Shannon entropy, relative entropy, or Renyi entropy.

14. The image analysis system of claim 10, wherein the one or more routines, when executed by the processor, cause the processor to display a simulated monochromatic image at the target monochromatic energy.

15. The image analysis system of claim 10, wherein generating the plurality of simulated monochromatic images comprises performing linear weighted combinations of the material density maps using the respective mass attenuation coefficients of respective materials as weights.

16. A non-transitory, computer-readable media, encoding one or more processor-executable routines, wherein the routines, when executed by a processor, cause acts to be performed comprising:
accessing at least a first image acquired using a first polychromatic spectrum and a second image acquired using a second polychromatic spectrum;
generating material density maps for at least two materials using the first image and the second image;
generating a plurality of simulated monochromatic images using the material density maps, wherein each simulated monochromatic image is at a different monochromatic energy;
generating a respective histogram for each simulated monochromatic image, wherein each histogram is characterized by a respective dispersion;
for each histogram, deriving a quantitative metric characterizing the respective dispersion;
evaluating the quantitative metrics of the histograms to determine the histogram where dispersion is minimized; and
identifying the monochromatic energy corresponding to the histogram where dispersion is minimized as a target monochromatic energy at which homogeneous tissue responses have the least variation.

17. The non-transitory, computer-readable media of claim 16, wherein determining the target monochromatic energy comprises:
computing an entropy metric as the quantitative metric for each distribution; and
identifying a minima in entropy with respect to monochromatic energy as the act of evaluating the quantitative metrics, wherein the minima is indicative of the target monochromatic energy.

18. The non-transitory, computer-readable media of claim 16, wherein the simulated monochromatic images correspond to a voxel, all or part of a slice, or a sub-volume of an imaged volume.

19. The non-transitory, computer-readable media of claim 16, wherein the routines, when executed by the processor, cause further acts to be performed comprising displaying a simulated monochromatic image at the target monochromatic energy.

20. The non-transitory, computer-readable media of claim 16, wherein the routines, when executed by the processor, cause further acts to be performed comprising displaying the target energy at every voxel for a sub-volume of an imaged volume.

* * * * *